United States Patent [19]

Sakai et al.

[11] Patent Number: 4,826,433
[45] Date of Patent: May 2, 1989

[54] STICK ABSORBER FOR ORAL CAVITY

[75] Inventors: Takashi Sakai; Hiroshi Kitayama, both of Toyama; Masamitu Yamamoto, Ehime; Takashi Mino, Ehime, all of Japan

[73] Assignees: Mitsubishi Acetate Co., Ltd., Tokyo; Uni-Charm Corp., Ehime, both of Japan

[21] Appl. No.: 62,549

[22] Filed: Jun. 16, 1987

[30] Foreign Application Priority Data

Jun. 16, 1986 [JP] Japan .................. 61-138367

[51] Int. Cl.⁴ .............................................. A61C 5/14
[52] U.S. Cl. .................................... 433/136; 604/370
[58] Field of Search ............... 433/136; 604/366, 370; 428/181, 172

[56] References Cited

U.S. PATENT DOCUMENTS

| 3,523,536 | 8/1970 | Ruffo ................................. 604/366 |
| 4,392,862 | 7/1983 | Marsan et al. ..................... 604/366 |
| 4,526,825 | 7/1985 | Whitehead ......................... 604/366 |
| 4,627,847 | 12/1986 | Puletti et al. ..................... 604/366 |
| 4,705,514 | 11/1987 | Barnard ............................. 433/136 |

Primary Examiner—John J. Wilson
Assistant Examiner—Adriene J. Lepiane
Attorney, Agent, or Firm—Sughrue, Mion, Zinn, Macpeak & Seas

[57] ABSTRACT

A stick absorber for the oral cavity comprising a bundle of fibers, the periphery of said bundle of fibers being wrapped with a water-permeable tape, and said tape being adhered at its joint with a binder. The stick absorber has high water absorbability and spacing effects, and does not release its constituent fibers into the oral cavity.

6 Claims, 2 Drawing Sheets

4,826,433

STICK ABSORBER FOR ORAL CAVITY

FIELD OF THE INVENTION

This invention relates to an absorber for the oral cavity which is useful for removal of undesired liquids, such as saliva, in dental treatment or to provide spacing in the oral cavity for dental or oral surgery.

BACKGROUND OF THE INVENTION

In dental or oral treatment or surgery, a piece of absorbent cotton which consists of short fibers has been used for removing liquids in the oral cavity, such as saliva, etc., for providing a space required for surgery, or for clenching. For increased convenience, absorbent cotton cut to an appropriate size or pre-fabricated in a stick or roll form is also available.

When using absorbent cotton, however, it is necessary to cut it or wad it into a ball, either at the time of use or in advance. Although a cut piece of absorbent cotton adequately cleans the oral cavity, it is nappy and leaves short fibers in the oral cavity. It is also unsatisfactory for providing a space required for surgery (spacing effect) due to its form collapse by wetting. While absorbent cotton fabricated in a stick form using an adhesive may improve these aspects, since the adhesive used for prevention of surface napping and retention of the shape on absorption of water, such as carboxymethyl cellulose, is water-soluble, such an adhesive is dissolved in saliva, etc., upon use, releasing short fibers into the oral cavity and reducing the spacing effect.

In an attempt to prevent napping and releasing fibers in the oral cavity, there have been proposed a stick absorber in which absorbent cotton in a stick form is covered on approximately half its peripheral surface with a film sparingly permeable to moisture and is further spirally coiled with a fine yarn, as disclosed in Japanese Utility Model Publication No. 21178/84, and an absorbent material in which a mixture of cotton pulp and a highly absorbent powdery substance is wrapped with a water-permeable film, as disclosed in Japanese Utility Model Publication No. 7708/85. However, the former has the disadvantages that short fibers constituting the stick are easily released from the gaps between turns of the fine yarn, and that the complicated process required for coiling may result in a low productivity. Although the latter hardly leaves fibers in the oral cavity and has excellent form retention properties on water absorption, it also requires the complicated production process, and may result in a low productivity and high production cost. Moreover, when it is swollen with water or pressed when it contains water, the absorbent substance contained therein leaks out to cause discomfort to patients.

SUMMARY OF THE INVENTION

Accordingly, one object of the invention is to provide a stick absorber for the oral cavity, having excellent water absorbability and spacing effect, which does not release its constituting fibers in the oral cavity.

Another object of the invention is to provide a stick absorber for the oral cavity which can be produced at a high productivity and a low cost.

These and other objects of the present invention have now been attained by a stick absorber for the oral cavity comprising a bundle of fibers, the periphery of which is wrapped with a water-permeable tape, and the tape being adhered at its joint with a binder.

DETAILED DESCRIPTION OF THE INVENTION

The fibers which can be used in the present invention preferably are filaments, such as acetate filaments, rayon filaments, polyester filaments, polypropylene filaments, and acrylic filaments. Among these, acetate filaments are more preferred. In order to obtain an absorber having a high void volume for assuring excellent absorbability or to make transverse wrinkles on the peripheral tape as hereinafter described, these filaments preferably have about 5 or more crimps per 25 mm length.

Substantially continuous filament fibers which are bundled in a stick form after opening, for example, a tow, are advantageously used as the fibers.

The water-permeable tape which can be used for wrapping the periphery of the bundle of fibers is preferably made of a water-permeable non-woven fabric composed of rayon, polyester fibers, polypropylene fibers, cellulose fibers, or conjugate fibers thereof. In particular, a non-woven rayon fabric is particularly preferred because of its soft texture and high water absorbability. To ensure form retention, the non-woven fabric used preferably has a wet strength at least 45 g/15 mm-width. Ordinary paper lacking this wet strength is unsuitable for use as a water-permeable tape in the present invention.

In a preferred embodiment of the present invention, the outer tape provided on the periphery of the bundle of fibers is wrinkled transverse to the lengthwise direction of the fibers. This embodiment gives a stick absorber excellent fitness in the oral cavity.

Figure 1:
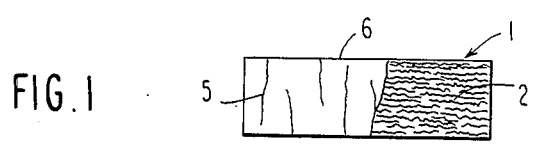
FIGS. 1 and 2 each illustrate a side view and a partial transverse section of an embodiment of the stick absorber according to the present invention.
Figure 2:
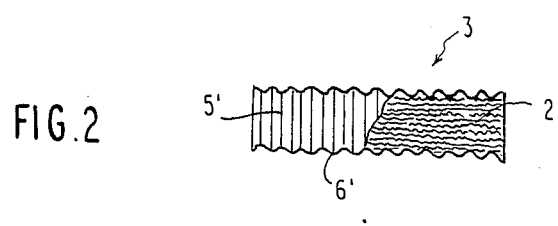

In the present invention, in order to form the wrinkles on the outer tape provided on the periphery of the bundle of fibers, two typical ways are given. One is a way in which a bundle of fibers is wrapped with a water-permeable tape while providing tension to the lengthwise direction of the fibers and after forming into a stick form, transverse wrinkles are formed on the tape by release of the tension. FIG. 1 shows an example of a stick absorber obtained by using this way. Another is a way in which a water-permeable tape is embossed with a continuous or discontinuous line pattern approximately transverse to the lengthwise direction of the tape to regulate swelling of the fibers. FIG. 2 shows an example of a stick absorber obtained by using this way.

Figure 3:
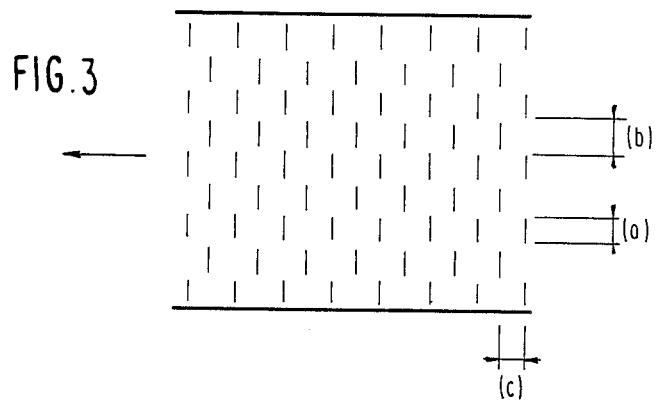
FIG. 3 shows an example of an embossed pattern formed on the water-permeable tape according to the present invention.

FIG. 3 shows an example of a tape having such an embossed pattern. In a more preferred embodiment, the embossed pattern comprises from 1 to 20 lines per cm that are approximately transverse to the lengthwise direction of the tape and arranged at a regular interval either continuously or discontinuously.

The embossed pattern may comprise dashes parallel to the lengthwise direction of the tape.

According to the present invention, at least both edges of the water-permeable tape wrapping around the bundle of fibers in the form of a stick are adhered with a binder as hereinafter described.

The binder which can be used at least in the joint formed by the tape edges is preferably water-insoluble so as not to be dissolved upon use in the oral cavity. Preferred water-insoluble binders include a hot-melt binder such as an ethylene-vinyl acetate copolymer. The hot-melt binders may be used without using any solvent. A fibrous hot-melt binder may be incorporated as a component of a water-permeable tape. For example, a water-permeable tape containing at least about 10% by weight of the fibrous hot-melt binder can be fused together at the joint by heat application by means of contact with a heater element, and the like. Suitable fibrous hot-melt binders include those consisting mainly or solely of at least one polymer such as polyethylene, polypropylene, polyester, polyamide, or a vinyl chloride-vinyl acetate copolymer as a low-melting component.

The absorber according to the present invention can be prepared by using, for example, a commonly employed apparatus for manufacturing cigarette filters (plug making machine) as follows. A tow that is a bundle of a large number of crimped filaments is first opened uniformly and then compressed into a cylindrical form in the garniture of the machine. A water-permeable tape is continuously wrapped around the periphery of the cylindrical fiber bundle. One edge of the tape is coated with a molten solution of a hot-melt binder and overlapped with the other edge of the tape, followed by cooling to solidify the binder. The resulting stick is then cut to a prescribed size. The cut stick, when released from the garniture of the machine (unloaded), shrinks in lengthwise and/or expands in cross-section direction due to elastic recovery of the crimped filaments. Particularly when the bundle of fibers is composed of crimped filaments and the water-permeable tape wrapping around the fiber bundle is soft, the degree of expansion increases due to greater elastic recovery of the filaments, to form transverse wrinkles on the tape provided on the periphery of the stick absorber. In the above-described preferred embodiment of the present invention where the water-permeable tape has a regular linear emboss, regular transverse wrinkles substantially corresponding to the embossed pattern can be formed on the tape transverse to the longitudinal axis.

FIGS. 1 and 2 each illustrate a side view of the above-described stick absorber, in which stick absorber 1 is composed of a bundle of fibers (tow) 2 comprising crimped filaments and a water-permeable tape 6 or 6' made of a non-woven rayon fabric tape. The numeral 5 in FIG. 1 indicates transverse wrinkles. Since the water-permeable tape used in the absorber of FIG. 2 has a regular discontinuous line emboss as shown in FIG. 3, transverse wrinkles 5' formed on surface of stick 3 are also regular.

The present invention will now be illustrated in greater detail by way of the following examples, but it should be understood that the present invention is not deemed to be limited thereto. In these examples, an apparatus for manufacturing cigarette filters (i.e., plug making machine) was employed for sample preparation.

EXAMPLE 1

A tow composed of diacetate crimped filaments having 21 crimps per 25 mm, a fineness of 3 denier and a Y-shape cross-section (36,000 denier in total) was opened uniformly and then fed into a garniture of a conventional plug making machine by compression to form a bundle of fibers in a cylindrical form. A non-woven fabric tape of rayon filaments having a basis weight of 35 g/m$^2$ and a wet strength of 190 g/15 mm width was used as a water-permeable tape in a width of 27 mm. The tape was fed into the garniture and wrapped around the periphery of the bundle of fibers. One edge of the tape was coated with a water-insoluble hot-melt binder comprising an ethylene vinyl acetate copolymer, overlapped on the other edge of the tape, and then cooled to solidify the binder at the joint. The resulting stick was cut to lengths of 30 mm to obtain stick absorbers. Wet strength was measured by using TENSILON UTM-II type strength measuring devise manufactured by Toyo Baldwin Co., Ltd.

When the stick was released from the stress by the garniture, it shrank in lengthwise and expanded in diameter so that the resulting stick absorber had a circumference of 31 mm and its outer periphery had an average of 3 fine wrinkles per cm of length substantially transverse to the longitudinal axis as shown in FIG. 1. This absorber was designated as Sample A.

EXAMPLE 2

Stick absorbers were prepared in the same manner as in Example 1, except for using a 25 cm wide tape cut from a non-woven rayon fabric having a basis weight of 26 g/m$^2$ and a wet strength of 170 g/15 mm width, on which broken lines composed of dashes 2 mm in length (a) separated by spaces 3 mm in length (b) were embossed at 2.5 mm interval (c) as shown in FIG. 3. The resulting stick absorber had a length of 30 mm and a circumference of 25 mm and there were formed on its outer periphery clear transverse wrinkles at a regular average interval of about 4.2 wrinkles per cm of length as shown in FIG. 2. This absorber was designated as Sample B.

Figure 4:
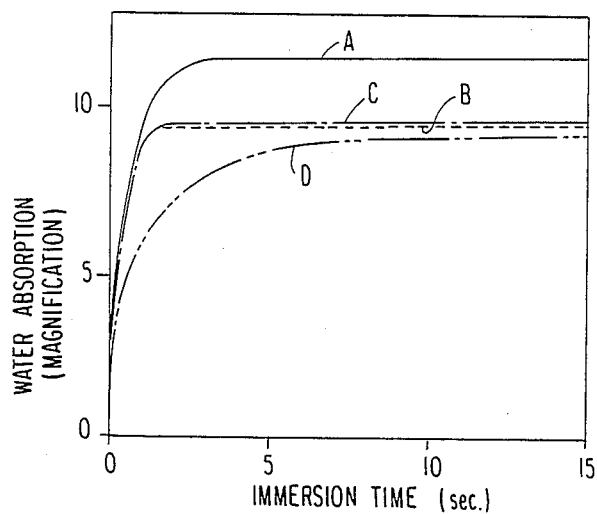
FIG. 4 is a graph showing water absorption vs. immersion time.
Figure 5:
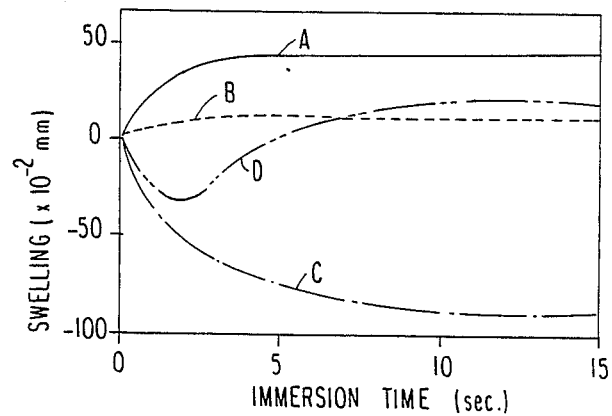
FIG. 5 is a graph showing swelling or collapse vs. immersion time.
Figure 6:
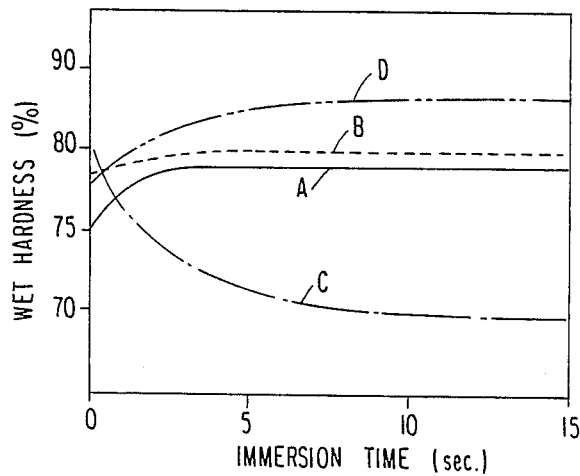
FIG. 6 is a graph showing the change of wet hardness vs. immersion time.

Each of Samples A and B was laid down on its side in a petri dish having an area of 110 cm$^2$ containing 45 cc of water. The water absorption, swelling, and hardness of the absorber were measured at intervals of time (1, 2, 3, 4, 5, 10, and 15 seconds each). For comparison, the same test was conducted using a commercially available cotton roll (Sample C) and the absorber of Japanese Utility Model Publication No. 7708/85, constructed of cotton pulp containing a highly water absorbent powdery substance wrapped in a water-permeable non-woven fabric (Sample D). The results obtained are shown in FIGS. 4, 5 and 6.

The water absorption was obtained by dividing the wet weight after water absorption by the dry weight before water absorption; the swelling (1/100 mm) was obtained by applying a load of 100 g to the side of a sample laid down on its side before and after water absorption and subtracting the height ($h_2$) of the dry sample before water absorption from that ($h_3$) of the wet sample after water absorption; and the wet hardness (%) was obtained by dividing ($h_3$) by the height ($h_0$) of a dry sample without any load and multiplying the quotient by 100. For reference, the dry weights of these samples before water absorption were as follows.

Sample A = 0.208 g

Sample B=0.178 g
Sample C=0.214 g
Sample D=0.316 g

As can be seen from the Figures, each of Sample A to D exhibited excellent water absorbency. However, Sample C was significantly collapsed by water absorption, and Sample D had a low rate of water absorption and also underwent shrinkage in the initial stage of water absorption. Further, when a load was applied to Sample D, the highly water absorbent powdery substance having absorbed water leaked out. In contrast, both Samples A and B were excellent in rate of water absorption, swellability, and hardness. When Samples A and B were tested by dentists for their usability, they were rated high in rate of water absorption, spacing effect, and freedom from release of fibers.

EXAMPLE 3

Cylindrical absorbers were produced in the same manner as in Example 1, except for using, as a fiber bundle, a tow composed of acetate crimped filaments each having a fineness of 3 denier and a Y-shape cross section (50,000 denier in total) and a 32 mm wide tape cut from a non-woven fabric having a basis weight of 35 g/m² and a wet strength of 240 g/15 mm width which was obtained by a dry process from a random web composed of 65% by weight of rayon cotton having a single fiber fineness of 3 denier and 35% by weight of hot-melt fibers. The hot-melt fibers used here were conjugate fibers having a single fiber fineness of 4 denier and comprising polyester having a melting point of 260° C. and polyethylene having a melting point of 130° C. The edges of the tape at the joint were adhered by heating with an iron bar heated to 165° C. After cooling with a water-cooling bar, the cylindrical absorber was cut to lengths of 30 mm to prepare stick absorbers having a diameter of 9.8 mm (hereinafter designated as Sample E). The rate of production was 2,000 stick absorbers per minute.

EXAMPLE 4

Stick absorbers were produced in the same manner as in Example 3, except for using, as a fiber bundle, a cotton sliver having a weight of 7 g/m and a 32 mm wide tape cut from a non-woven fabric having a basis weight of 30 g/m² and a wet strength of 370 g/15 mm width which was obtained by a dry process from a random web comprising 30% by weight of rayon having a single fiber fineness of 3 denier, 20% by weight of polyester fiber having a single fiber fineness of 4 denier, and 50% by weight of hot-melt fibers. The hot-melt fibers used here were conjugate fibers having fineness of 4 denier and comprising polyester having a melting point of 260° C. and polyester having a melting point of 130° C. The resulting stick absorbers had a diameter of 9.6 mm and a length of 30 mm (hereinafter designated as Sample F). The rate of production was 1,000 stick absorbers per minute.

Each of Samples E and F and, as a comparative sample, a commercially available cotton roll having a diameter of 8.6 mm and a length of 30 mm (designated as Sample G) was laid on its side in a petri dish containing water for 5 minutes to evaluate water absorption characteristics. The results obtained are shown in Table 1 below.

In Table 1, the water absorption was obtained in the same manner as in Examples 1 and 2. The dry hardness was obtained by dividing ($h_2$) (load: 300 g) by ($h_0$) and multiplying the quotient by 100, and the wet hardness was obtained by dividing ($h_3$) (load: 300 g) by ($h_0$) and multiplying the quotient by 100.

TABLE 1

|  | Sample E | Sample F | Sample G |
| --- | --- | --- | --- |
| Dry Weight (g) | 0.223 | 0.269 | 0.228 |
| Wet Weight (g) | 2.473 | 2.620 | 1.985 |
| Water Absorption | 11.1 | 9.7 | 8.7 |
| Dry Hardness (%) | 43.5 | 63.7 | 57.1 |
| Wet Hardness (%) | 49.8 | 48.0 | 41.9 |

As described above, the stick absorber for the oral cavity in accordance with the present invention is excellent in water absorbability, spacing effect, and usefulness in the oral cavity and does not release constituting fibers in the oral cavity.

While the invention has been described in detail and with reference to specific embodiments thereof, it will be apparent to one skilled in the art that various changes and modifications can be made therein without departing from the spirit and scope thereof.

What is claimed is:

1. A stick absorber for the oral cavity comprising a bundle of crimped filaments, the periphery of said bundle of crimped filaments being wrapped with a water-permeable tape having an embossed pattern of lines substantially transverse to the absorber's length at substantially regular intervals, and said tape being adhered at its joint with a water-insoluble binder.

2. A stick absorber as in claim 1, wherein transverse wrinkles are formed on the tape provided on the bundle's periphery.

3. A stick absorber as in claim 1, wherein said filaments are acetate filaments.

4. A stick absorber as in claim 1, wherein said filaments have at least 5 crimps per 25 mm length.

5. A stick absorber as in claim 1, wherein said embossed pattern contains from 1 to 20 lines per cm in the length wise direction.

6. A stick absorber as in claim 1, wherein said water-insoluble binder is a hot melt binder.

* * * * *